United States Patent
Nash et al.

(10) Patent No.: US 6,569,151 B1
(45) Date of Patent: May 27, 2003

(54) DEVICE FOR CONNECTING A CATHETER OR OTHER TUBULAR MEMBER ONTO A GUIDE-WIRE WITHOUT ACCESS TO THE ENDS OF THE GUIDE-WIRE

(75) Inventors: John E. Nash, Chester Springs, PA (US); William T. Fisher, Schwenksville, PA (US); H. Michael Cunningham, Phoenixville, PA (US); Gregory Walters, Malvern, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

(21) Appl. No.: 09/523,077

(22) Filed: Mar. 10, 2000

(51) Int. Cl.[7] .................. A61M 25/16; A61M 25/18; A61M 39/00; A61M 39/10
(52) U.S. Cl. .................. 604/533; 604/30; 604/103; 604/236; 604/247
(58) Field of Search .................. 116/234; 128/637; 600/567; 606/185, 213; 623/1.11; 604/96, 165

(56) References Cited

U.S. PATENT DOCUMENTS

| | | | | |
|---|---|---|---|---|
| 4,771,782 A | * | 9/1988 | Millar | 128/637 |
| 4,946,443 A | | 8/1990 | Hauser et al. | |
| 5,016,559 A | * | 5/1991 | Larson et al. | 116/234 |
| 5,267,958 A | | 12/1993 | Buchbinder et al. | |
| 5,324,306 A | * | 6/1994 | Makeower et al. | 606/213 |
| 5,752,970 A | * | 5/1998 | Yoon | 606/185 |
| 6,007,517 A | | 12/1999 | Anderson | |
| 6,022,336 A | | 2/2000 | Zadno-Azizi et al. | |
| 6,086,543 A | * | 7/2000 | Anderson et al. | 600/567 |
| 6,156,062 A | * | 12/2000 | McGuinness | 623/1.11 |

* cited by examiner

*Primary Examiner*—Henry Bennett
*Assistant Examiner*—Sabrina Dagostino
(74) *Attorney, Agent, or Firm*—Caesar, Rivise, Bernstein, Cohen & Pokotilow, Ltd.

(57) ABSTRACT

A tubular instrument, e.g., a catheter including a hollow wall portion forming the distal end of the instrument and terminating at a distal opening, having a connector arranged to be used with a guide-wire. The guide wire has a distal end portion and a proximal end portion, the distal end portion of the guide-wire being arranged to be extended to some interior position within the body of a living being, with the proximal end portion of the guide-wire being located outside the being's body. The connector is located at the distal end of the instrument and is arranged to be readily manipulated by a twisting action to connect the instrument onto the guide-wire for sliding movement therealong. In particular, the connector establishes a path into which a portion of the guide-wire can be inserted from a lateral direction by merely twisting the instrument, without requiring access to either end of the guide-wire. In one embodiment the path is a spiral channel formed in the hollow wall portion of the instrument. In another embodiment the connector is a spiral member located on the outside of the distal end of the instrument, spaced slightly from the outer surface of the instrument to form the path or channel into which the guide-wire is inserted.

25 Claims, 4 Drawing Sheets

DEVICE FOR CONNECTING A CATHETER OR OTHER TUBULAR MEMBER ONTO A GUIDE-WIRE WITHOUT ACCESS TO THE ENDS OF THE GUIDE-WIRE

FIELD OF THE INVENTION

This invention relates generally to medical devices and more particularly to devices for use with catheters or other tubular devices that are arranged to be located at some intra-lumenal, e.g., intra-vascular, position within the body of a being by a conventional guide-wire or other guide member.

BACKGROUND OF THE INVENTION

Heretofore the mounting of a tubular instrument, e.g., a catheter, on a guide-wire has typically required access to either the distal or the proximal end of the guide-wire. Where the guide-wire is already in place, access has been achieved by mounting the instrument on the proximal end of the guide-wire and then sliding it into place over or along the guide-wire. For example, the so-called "over-the-wire" catheter (such as a balloon angioplasty catheter) has a central or other longitudinal extending passageway therethrough arranged to receive the guide-wire. In particular, the passageway of such a catheter is introduced on the proximal end of the guide-wire and then the catheter is slid down the guide-wire to the desired location. The advantage of this type of instrument and guidance system is that it can have a relatively small cross-sectional area or "crossing-diameter," a feature of some importance in applications wherein the lumen being traversed is small, e.g., an artery occluded by atherosclerotic deposits. The so-called "mono-rail" catheter doesn't make use of a central passageway for receipt of the guide-wire, but instead makes use of some externally located connector located on the distal end of the catheter and arranged to receive the guide-wire through it. The mono-rail catheter is also arranged to be introduced on the proximal end of the guide-wire, but outside the guide-wire so that the guide-wire passes through the connector on the distal end of the catheter, with the catheter itself being located beside the guide-wire so that it can be slid along the guide-wire to the desired location.

As will be appreciated by those skilled in the art, if the proximal end of the guide-wire has some structure permanently or transiently mounted or secured on it, e.g., a twist or torque handle (for rotating the guide-wire to a desired angular orientation), a valve (to enable some gas to be introduced through the guide-wire, such as to inflate a balloon on the distal end of the guide-wire), another catheter, etc., that is of a relatively large diameter or cross-sectional area, such a proximally mounted structure would necessarily impede the mounting of the instrument over the guide-wire once the guide-wire is in place within the being's body.

In U.S. Pat. No. 6,022,336 (Zadno-Azis et al.) there is disclosed a catheter system for revascularizing an occluded vessel and for containing any emboli produced during the use of the system. As best seen in FIGS. 7 and 10A of that patent the instrument makes use of plural catheters for providing at least one pair of paths for irrigation and aspiration fluid flow. One of the catheters, designated as an "intermediate" catheter includes an externally mounted lumen structure for receipt of an inner catheter therethrough. This lumen structure may include a longitudinally extending slit or weakened area along the entire length of the lumen structure to facilitate faster and easier insertion and removal of the inner catheter through the side wall of the lumen structure. By inserting and removing the inner catheter through the slit in the side wall of the lumen structure, the need to remove adapters and attachments from the proximal end prior to slidably advancing or removing the intermediate catheter over the inner catheter is eliminated. Thus, this lumen structure which is mounted at the distal end of the intermediate catheter for accommodating the inner catheter enables the intermediate catheter to be guided along the inner catheter in a manner like the heretofore discussed mono-rail catheters are slid along a guide-wire. However, unlike the prior art devices for mounting an instrument on a guide-wire in a mono-rail like arrangement, the device of Zadno-Azizi et al. patent does not require access to the proximal end of the intermediate catheter or guide-wire. Instead the device of the Zadno-Azizi et al. patent enables the inner catheter to be inserted laterally into a longitudinally extending access slit in the lumen structure at a intermediate location along the inner catheter. By inserting and removing the inner catheter through the slit in the side wall of the lumen structure on the distal end of the intermediate catheter, the need to remove adapters and attachments from the proximal end of the intermediate catheter prior to slidably advancing or removing that catheter over the inner catheter is eliminated.

While the instrument of the Zadno-Azizi et al. patent appears generally suitable for its intended purposes, it appears to leave something to be desired from various standpoints. For example, since the lumen structure with the access slit is located externally to the intermediate catheter it will necessarily add its diameter to the diameter of the intermediate catheter, thereby limiting its usefulness to relatively large crossing diameter lumens. Also, the manner in which the intermediate catheter is attached or mounted onto the inner catheter or guide-wire may be somewhat difficult to achieve, and the additional structure, e.g., the slit bearing lumen structure, on the distal end could cause the distal end to get snagged on stents placed in the vessel. Further still, since the slit through which the inner catheter or guide-wire is inserted is linear and extends longitudinally, the inner catheter or guide-wire may come out of the lumen during the traversal of difficult anatomical orientations, e.g, tortuous vascular paths.

OBJECTS OF THE INVENTION

Accordingly, it is a general object of this invention to provide a catheter or other instrument including a connector to be used on a guide-wire or other elongated guide member extending into the body of a living being that overcomes the disadvantages of the prior art.

It is another object of this invention to provide a catheter or other instrument that includes connector for slidably securing the catheter or other instrument with respect to a guide-wire or other elongated guide member and that is simple in construction.

It is another object of this invention to provide a catheter or other instrument that is easy to mount on a guide-wire or other elongated guide member.

It is another object of this invention to provide a catheter or other instrument which enables the ready placement of the catheter or other instrument at a desired location within the body of a living being;

It is another object of this invention to provide a catheter or other instrument that easy to use with a guide-wire or other elongated guide member to effect the desired placement of the catheter or other instrument into a desired position within the body of a living being.

It is another object of this invention to provide a catheter or other instrument having a connector to connect the catheter or other instrument to a guide-wire or other elongated guide member and which is resistant to accidental disconnection therefrom.

It is another object of this invention to provide a catheter or other instrument including a connector to be used on a guide-wire or other elongated guide member that exhibits a small crossing-diameter.

It is another object of this invention to provide a connector for a catheter or other instrument which achieves the foregoing objects.

SUMMARY OF THE INVENTION

A tubular instrument, e.g., a catheter including a hollow wall portion forming the distal end of the instrument and terminating at a distal opening, having a connector arranged to be used with, e.g., guided by, a guide-wire or other elongated guide member. The guide-wire/elongated guide member may be a conventional device having a distal end portion and a proximal end portion, the distal end portion of the guide-wire/elongated guide being arranged to be extended to some interior position within a lumen e.g., an occluded artery, in the body of a living being, with the proximal end portion of the guide-wire/elongated guide member being located outside the body of the being. The connector is arranged to connect the instrument to the guide-wire/elongated guide member by twisting it onto the guide-wire/elongated guide member, so that the instrument can be guided to a desired position within the body of the being thereby.

The connector, e.g., a releasably securable connector, is located at the distal end of the instrument and establishes a path into which a portion of the guide-wire/elongated guide member can be inserted from a lateral direction, without requiring access to either end of the guide-wire/elongated guide member.

In accordance with one preferred embodiment of the invention the path is a channel formed in the hollow wall portion of the instrument and communicating with the opening therein, e.g., a helical channel having a proximal end, and a distal end in communication with the opening in the distal end of said instrument. In this embodiment the distal end of the channel is arranged to initially receive the guide-wire/elongated guide member so that the guide-wire/elongated guide member can be inserted into the channel when the instrument is twisted, causing the guide-wire/elongated guide member to extend through the opening in the distal end of the instrument, through a portion of the instrument, and out of the proximal end of the channel.

In accordance with another, albeit less, preferred embodiment of the invention the path is a channel formed by a member located on the outside of the distal end of the instrument, e.g., a helical wire which has a distal end and a proximal end, with the distal end of the helical wire being secured to the distal end portion of the instrument and with the proximal end of the helical wire being free and spaced slightly from said instrument to form a channel therebetween having an entrance mouth into which the guide-wire/elongated guide member can be inserted, whereupon the guide-wire/elongated guide member extends between the helical wire and the instrument and out of the proximal end of the channel.

DETAILED DESCRIPTION OF THE PREFERRED EMBODIMENT

Figure 1:
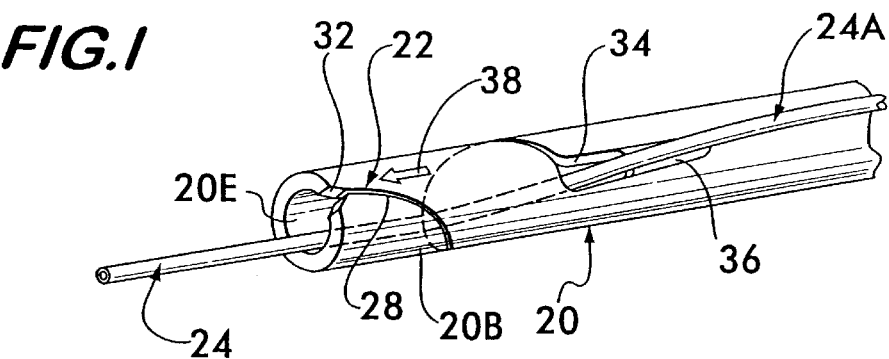
FIG. 1 is an isometric view of the distal end of one embodiment of a catheter constructed in accordance with this invention and shown after it has been mounted on a conventional guide-wire by a helical connector forming a portion of the distal end of the catheter.

Referring now to the various figures of the drawing wherein like reference characters refer to like parts, there is shown at 20 in FIG. 1 the distal end of a tubular instrument, such as an infusate catheter for use in a intravascular revascularization system, and having a connector 22 constructed in accordance with one embodiment of this invention for quickly and easily securing the catheter 20 onto a conventional guide-wire 24 without requiring access to either end of the guide-wire.

Before discussing the details of the connector 22, it should be pointed out that the subject invention can be used with any type of tubular instrument, be it a catheter or otherwise, that is arranged to be extended along a guide-wire or other elongated guide member into the body of a living being to a desired location and without requiring access to either end of the guide-wire or other elongated guide member. In the embodiments shown herein the guide-wire 24 is shown as being a tubular member, but can, if desired be a solid wire.

Figure 7:
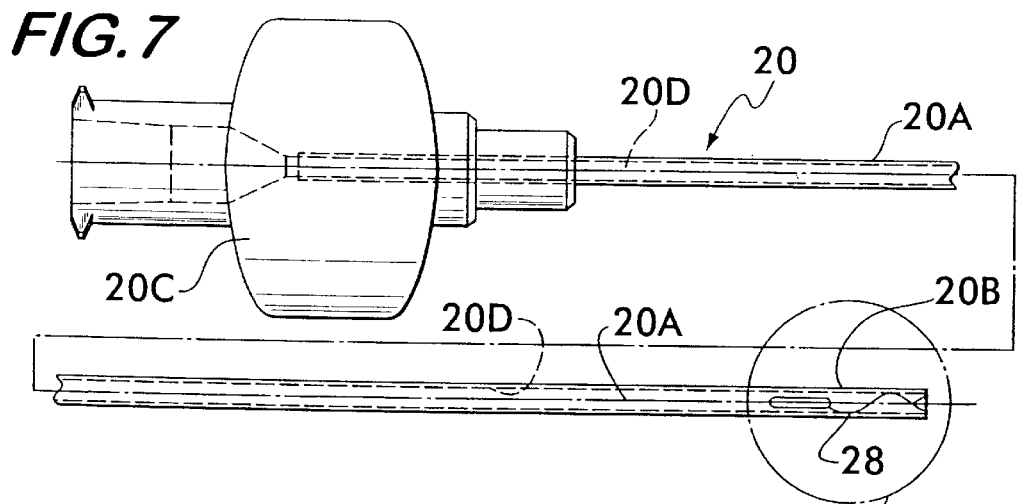
FIG. 7 is a reduced top plan view of the embodiment of the catheter shown in FIG. 1.
Figure 8:
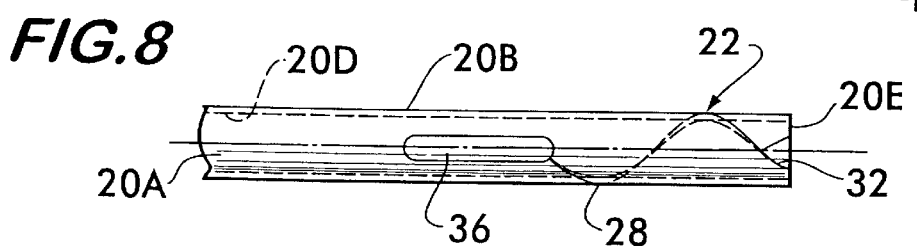
FIG. 8 is an enlarged top plan view of the portion of the embodiment of the catheter shown within the area bounded by the circular broken line in FIG. 7.

The infusate catheter whose distal end is shown in FIG. 1 is shown fully in the plan view of FIG. 7 and is merely exemplary of any type of catheter or tubular instrument for which the subject invention has application and utility, e.g., an angiographic catheter. As best seen in FIG. 7 the catheter 20 basically comprises an elongated tubular body 20A terminating at a distal end 20B at which the connector 22 of the subject invention is located. The opposite or proximal end of the catheter 22 is in the form of an enlarged hub or connector 20C for connection to the associated components of the revascularization system (not shown). A central passageway 20D extends through the catheter and terminates at an open free end 20E (FIGS. 7 and 1). In the exemplary embodiment of catheter 20, the passageway 20D is arranged to carry an infusate liquid therethrough for ejection via opening 20E into the portion of the vessel being revascularized or diagnosed.

Turning now to FIG. 1 the details of the connector 22 will now be considered. As can be seen the connector is in the form of a helical channel 28 cut into the wall 30 of the catheter at the distal end portion 20B so that it is in communication with the interior passageway 20D of the catheter along the entire length of the channel. The channel 28 may be of fixed or variable pitch and includes a widened or flared mouth 32 where it meets or merges with the open free end 20D of the catheter. It is through this mouth that the guide-wire is inserted into the channel. The proximal end of the channel 28 terminates in an elongated slot or exit window 34 that is also in communication with the interior passageway 20D. It is through the window 34 that the guide-wire exits the channel. Thus, the channel forms a path into which the guide-wire can be inserted to slidingly connect the catheter to the guide-wire. As will be discussed in detail to follow, the path is constructed so that the entry of the guide-wire into and through it can be facilitated easily, quickly and reliably with only a slight twisting action.

In accordance with one preferred aspect of this invention the material making up the catheter is preferably resilient so that the guide-wire 24 can be extended into the mouth 32 of the channel and then into contiguous portion of the channel 28, whereupon the channel flexes open somewhat to enable the guide-wire to pass therethrough to exit from the window 34. As the guide-wire moves proximally along the channel to the window 34, portions for the channel distally of the guide wire flexes back to the initial position, whereupon when the guide-wire is within the window, the channel will have assumed its unflexed or normally closed condition. It should, however, be pointed out at this juncture that the catheter or the material forming slot need not be resilient, so long as the slot can accommodate the guide-wire therein to enable it to slide with respect thereto, as will be described later.

Figure 2:
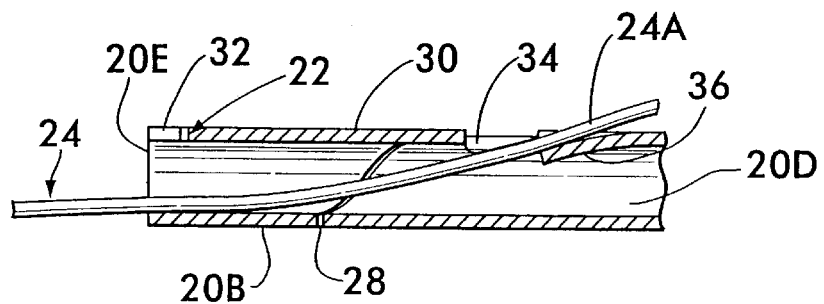
FIG. 2 is a longitudinal sectional view of the distal end of the embodiment of the catheter shown in FIG. 1.

In order to facilitate the exit of the guide-wire 24 from the channel 28 at the window 34 and to ensure that the guide-wire extends closely parallel to the outer surface of the catheter from its exit point proximally, an elongate recess or depression 36 is formed in the wall 30 of the catheter 20 immediately proximally of the window 34. The recess 36 extends along an axis parallel to the longitudinal axis of the catheter and, as best seen in FIG. 2, inclines upward from its lowest point where it merges with the proximal end of the window 34 to the point where it terminates at the outer circular surface of the catheter proximally of the window.

In the exemplary embodiment shown the outer diameter of the catheter is approximately 0.05 inch. The spiral channel 20 forms at least one complete revolution about the periphery of the catheter so that the entry mouth 32 is axially aligned with the exit window 34. The width of the entrance mouth is approximately 0.025 inch. The width of the exit window is greater than the width of the channel 28, e.g., 0.02 inch versus 0 to 0.015 inch. The length of the channel 28 measured longitudinally from the open end 20E of the catheter to the proximal end of the window 34 (i.e., the lowest point of the recess 36) is approximately 0.25 inch.

In order to enable the user of the catheter to orient it in the desired rotational attitude for mounting onto the guide-wire, a process to be discussed in detail later, an indicator marker or indicia, such as an arrow 38, is provided on the catheter aligned with the flared mouth 32 so that the user of the catheter can readily determine the location of the channel's mouth 32 by viewing the indicator arrow 38.

Figure 10:
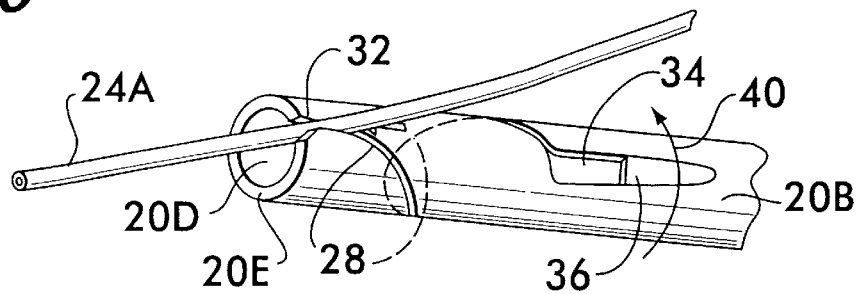
FIG. 10 is an isometric view similar to FIG. 9 but showing the distal end of the embodiment of the catheter of FIG. 1 during an intermediate step in the mounting of the catheter on the guide-wire.
Figure 11:
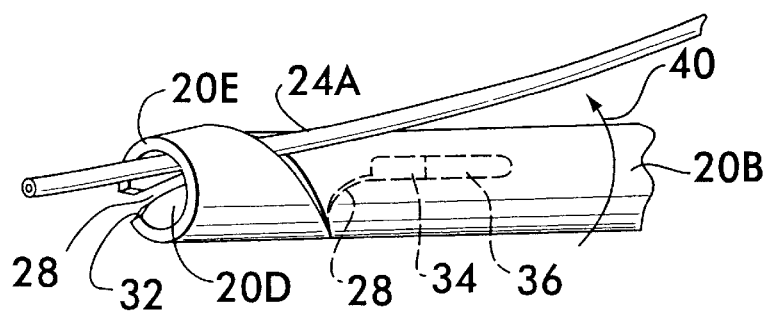
FIG. 11 is an isometric view similar to FIGS. 9 and 10 but showing the distal end of the embodiment of the catheter of FIG. 1 at a still later step in the mounting of the catheter on the guide-wire.

The mounting of the catheter 20 on the guide-wire 24 will now be discussed with reference to FIGS. 9–11. It is assumed that the guide-wire is already in place so that its distal end (not shown) is located at some internal situs within the body of the being, while its proximal end is located outside the body of the being, with some intermediate portion, designated by the reference number 24A herein, also being located outside the body of the being distally of the proximal end of the guide-wire. It is at this intermediate position that the catheter 20 is mounted on the guide-wire using the connector 22. It should be pointed out at this juncture that while the portion 24A of the guide-wire is preferably outside the body of the being, such an arrangement is not required. In this regard in some medical applications the guide wire portion 24A where the catheter is to be connected may be located internally of the being and access provided to it via a natural body orifice or opening or through some surgically formed opening.

Figure 9:
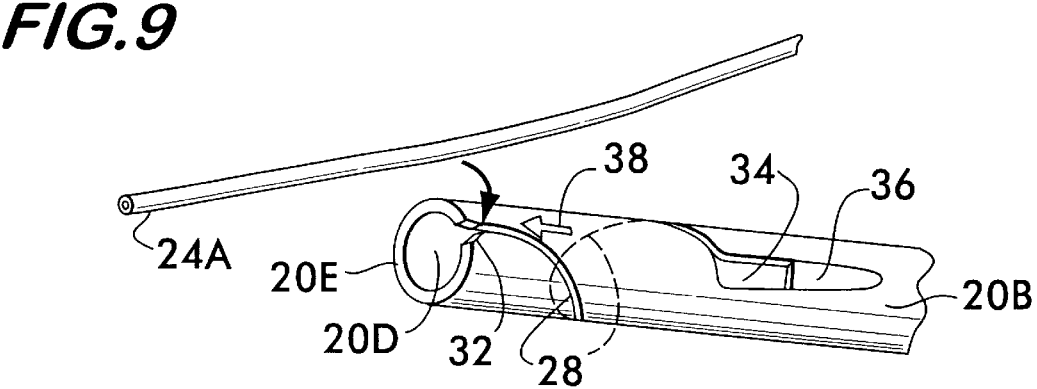
FIG. 9 is an isometric view of the distal end of the embodiment of the catheter shown in FIG. 1 during an initial step in the mounting of the catheter on the guide-wire.

In any case, as best seen in FIG. 9 the catheter 20 is oriented or twisted so that the entry mouth 32 at the distal end of the channel is aligned with the portion 24A of the guide-wire 24. The arrow indicia 38 facilitates the correct orientation alignment procedure. Once aligned the distal end of the catheter 20 is moved in a lateral direction (e.g., from the side of the guide-wire) toward it (or the guide-wire is moved toward the catheter) so that the guide-wire portion 24A enters into the mouth of the channel 116. Then the catheter is twisted or rotated in the direction shown by arrow 40 to cause the guide-wire portion 24A to enter into the contiguous portion of the channel 28, whereupon the channel flexes open, as described earlier. Continued twisting of the catheter in the direction of arrow 40 causes the guide-wire to move further down the channel as shown in FIG. 11. Continued twisting of the catheter with respect to the guide-wire in the direction of arrow 40 eventually brings the guide-wire portion 24A into the exit window 32, as shown in FIGS. 1 and 2, whereupon the guide-wire portion 24 exits the window and is guided upward by the inclined recess 36 until it is generally parallel to the outer surface of the catheter 20 (as best seen in FIG. 1). Once this has been accomplished, the catheter can be slid or moved in the distal direction along the guide-wire to bring the open distal end 20E of the catheter to the desired position within the being's body, e.g., at a situs of the atherosclerotic deposit to be removed.

Figure 3:
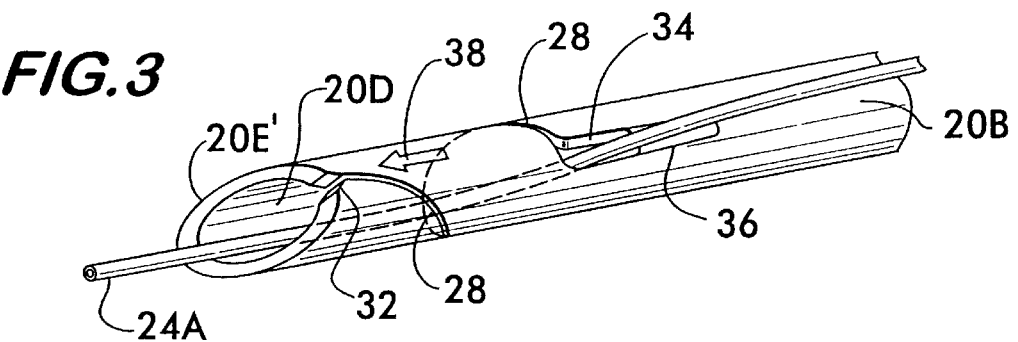
FIG. 3 is an isometric view of the distal end of another embodiment of a catheter, e.g., a beveled distal end catheter, constructed in accordance with this invention and shown after it has been mounted on a conventional guide-wire by a "helical-cut" connector forming a portion of the distal end of the catheter.
Figure 4:
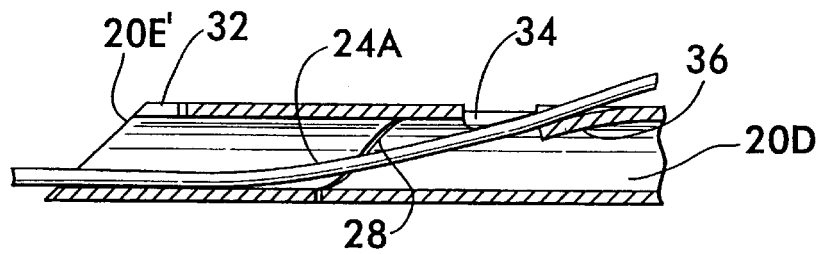
FIG. 4 is a longitudinal sectional view of the distal end of the embodiment of the catheter shown in FIG. 3.

In FIGS. 3 and 4 there is shown an alternative embodiment of a catheter 20' constructed in accordance with this invention. The catheter 20' is in all material respects identical to the catheter 20, except for the shape of its distal end.

Thus, in the interest of brevity the details of the construction and the operation of the catheter 20' will not be reiterated and the same reference numbers will be given to the common components. As can be seen in FIGS. 3 and 4 the distal end of the catheter 20' includes a beveled end 20E'. The entry mouth to the channel 28 is located on the most proximal portion of the beveled end 20E' for initial receipt of the guide-wire portion 24A therein.

Figure 5:
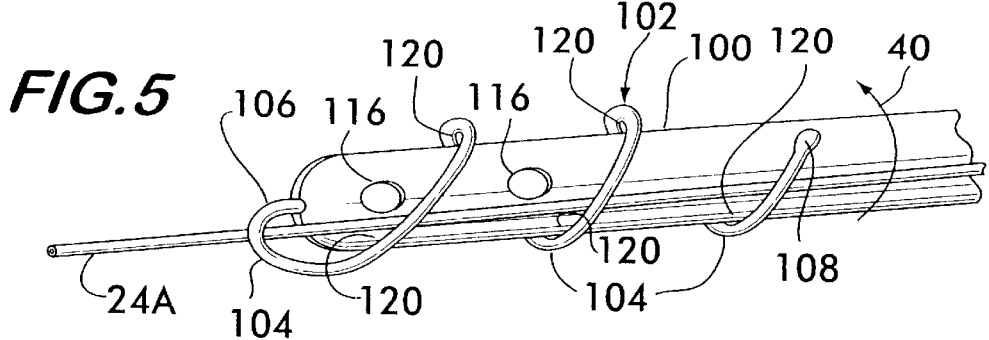
FIG. 5 is an isometric view of the distal end of still another embodiment of a catheter constructed in accordance with this invention and shown after it has been mounted on a conventional guide-wire by a "pigtail" connector forming a portion of the distal end of the catheter.
Figure 6:
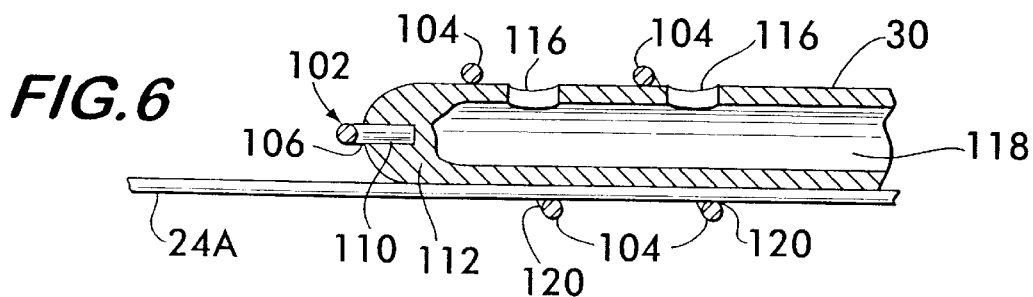
FIG. 6 is a longitudinal sectional view of the distal end of the embodiment of the catheter shown in FIG. 5.

In FIGS. 5 and 6 there is shown another embodiment of a catheter 100 constructed in accordance with this invention. The catheter 100 also includes a connector 102 (to be described in detail hereinafter) for facilitating the mounting of the catheter on a portion 24A of the guide-wire from a lateral or side direction and without requiring access to either end of the guide-wire. However, unlike the embodiments of FIGS. 1–4, the connector 102 of the catheter 100 is located externally to the outer surface of the distal end of the catheter 100 to form the path or channel for the guide-wire therebetween.

The connector 102 basically comprises a helical wire having plural consecutive helices 104 and terminating at one end in a distal end portion 106 and at the opposite or proximal end portion 108. The distal end portion 108 is linear and is centrally disposed within the helices 104 (See FIG. 6). The distal end portion is arranged to be fixedly secured in a central bore 110 in the distal end of the catheter 100. As can be seen the distal end of the catheter is closed, e.g., it includes a dome-shaped end wall 112 into which the bore 110 extends. Since the end of the catheter 100 is closed, if it is to be used as an infusating device it includes plural outlet ports or openings 116 extending through the sidewall 30 of the distal end portion and in communication with the central passageway 118 of the catheter. The helices 104 extend backward from the distal end portion 106 of the connector 102 and about the periphery of the outer surface of the catheter 100 to form an annular space or channel 120 therebetween. The thickness of the channel is just slightly greater than the outside diameter of the guide-wire (for reasons to be explained later). The proximal end portion 108 terminates in a somewhat bulbous free end 122 which is also spaced from the outer surface of the catheter and which forms the entry mouth for the channel 120. The connector 102 may be formed of any suitable biocompatible material, e.g., stainless steel, plastic, etc.

The mounting of the catheter 100 on the guide-wire portion 24A is accomplished by orienting or aligning the catheter 100 so that the guide-wire portion can be inserted into the entry mouth, i.e., the space between the bulbous distal free end 122 of the connector 102 and the outer surface of the catheter 100. Once aligned the distal end of the catheter 100 is moved in a lateral direction (e.g., from the side of the guide-wire) toward it (or the guide-wire is moved toward the catheter) so that the guide-wire portion 24A enters into the mouth of the channel 120. Then the catheter 100 is twisted or rotated in the direction shown by arrow 40 to cause the guide-wire portion 24A to enter into the contiguous portion of the channel 120, i.e., the helical portion defined by the helix closest to the free end 122. Continued twisting of the catheter in the direction of arrow 40 causes the guide-wire to move further down the channel, guided by the helices 104 until it exits from the channel at the distal most helix 104. At this time the guide-wire will be within the confines of the channel and disposed parallel to and very closely adjacent to the outer surface of the catheter. Once this has been accomplished, the catheter 100 can be slid or moved in the distal direction along the guide-wire 24 to bring the distal end of the catheter to the desired position within the being's body, e.g., at a situs of the atherosclerotic deposit to be removed.

In accordance with one preferred aspect of this invention the diameter of the wire making up the connector 102 is quite small, e.g., 0.010 inch, and the thickness of spacing between the inner surfaces of the connector's helices 102 and the outer surface of the catheter 100 (i.e., the thickness of the annular channel 120) is just slightly larger than the outside diameter of the catheter. Thus, the catheter 100 with the connector 102 thereon will still exhibit a small crossing diameter (albeit somewhat greater than a comparable diametrically sized catheter making use of the connectors like shown in FIGS. 1–4).

Figure 12:
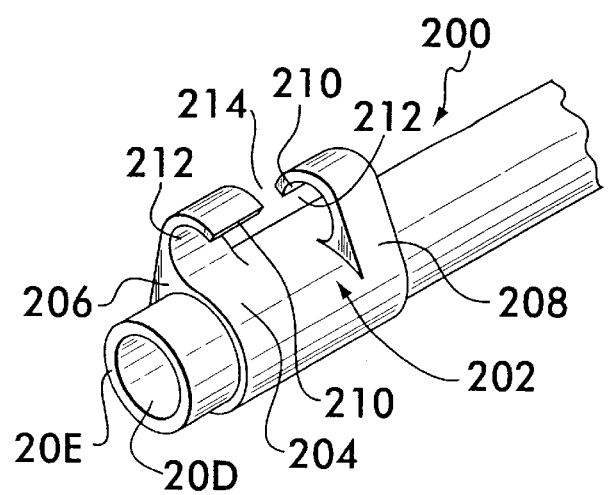
FIG. 12 is an isometric view of the distal end of another embodiment of a catheter constructed in accordance with this invention.
Figure 13:
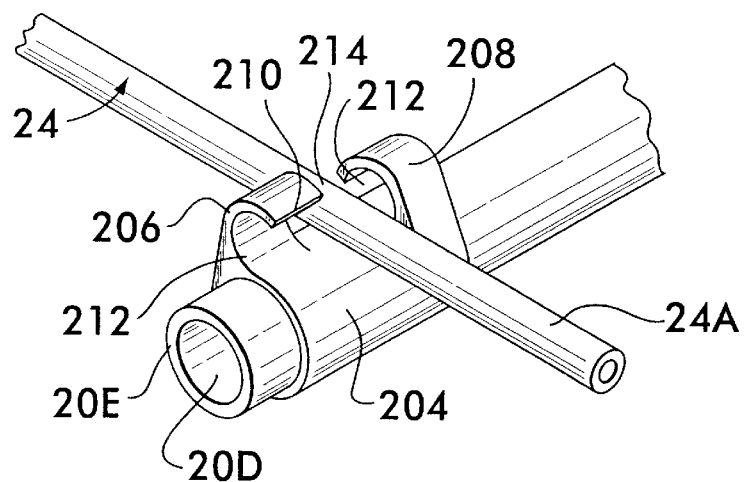
FIG. 13 is an isometric view similar to FIG. 12 but showing the distal end of the embodiment of the catheter of FIG. 12 during an initial step in the mounting of the catheter on a guide-wire.
Figure 14:
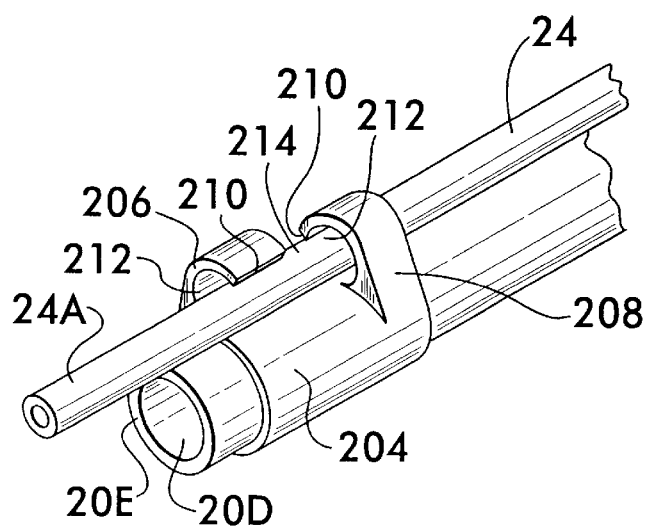
FIG. 14 is an isometric view similar to FIGS. 12 and 13 but showing the distal end of the embodiment of the catheter of FIG. 12 after the catheter has been mounted on the catheter on the guide-wire.

In FIGS. 12–14 there is shown yet another alternative embodiment of a catheter 200 constructed in accordance with this invention. The catheter 200 is similar to the catheter 20 in that it is a hollow tubular member having a central passageway 20D terminating at an open distal end 20E, yet is also similar to the catheter 100 in that catheter 200 includes an externally located connector 202. The connector 202 is like the other connectors described heretofore arranged to enable a guide wire 24 or other elongated guide member to be readily connected to the catheter by inserting it into a path (to be described hereinafter) by a twisting action, whereupon the catheter or other instrument can be slid along the guide-wire or other elongated guide member, yet is resistant to accidental disconnection.

As can be seen the connector 202 basically comprises a sleeve 204 formed of any biocompatible material, like those described heretofore, and having a pair of fingers 206 and 206 projecting outward therefrom. The sleeve 204 includes a circular central passageway whose inside diameter is approximately the same as the outside diameter of the distal end portion of the catheter 200 to accommodate that portion of the catheter extending therethrough. The sleeve is secured in place by any suitable means, e.g., an adhesive, by friction fit, etc. Moreover, the sleeve may be integrally formed on the distal end portion of the catheter. In fact, as will be appreciated from the discussion to follow, the use of a sleeve may be eliminated if the connector is formed integrally with the catheter. In such an arrangement, all that is required is that distal end of the catheter include the fingers 206 and 208 to form the guide-wire receiving path.

Each of the fingers 206 and 208 projects outward from the longitudinal axis of the connector and the longitudinal axis of the distal end of the catheter 200. Each of the fingers includes an overhanging, e.g., arcuate, free end 210. The free end of the respective fingers are directed in opposed directions to each other, i.e., they are directed so that they face each other but are offset from each other in the longitudinal direction. In particular, the free end 210 of the finger 206 is directed from one side of the catheter 200 towards the free end 210 of the finger 208 on the other side of the catheter. The fingers 206 and 208 may extend tangentially, radially or at some other orientation away from the central longitudinal axis of the catheter 200 so that the free end 210 of the finger 206 and the free end 210 of the finger 208 each form a respective portion of a channel or path 212 between them and the portion of the sleeve from which they project (or from the portion of the catheter from which they project if no sleeve is utilized, e.g., the fingers are formed integrally with the catheter 200.

In the preferred embodiment shown herein the path 212 is of a generally circular cross-section and extends linearly along the longitudinal axis of the catheter immediately adjacent the outer surface of the sleeve 204. It is in this channel or path 214 that the guide-wire portion 24A of the guide-wire 24 is arranged to be inserted to slidingly mount the catheter on the guide-wire. In accordance with a preferred embodiment of this invention the free ends 210 of the fingers 206 and 208 extend around the periphery of the guide-wire so that the fingers and contiguous portion of the sleeve each engage or encircle more than 180 degrees of the periphery of the guide-wire when the guide-wire is within the path or channel to prevent the guide-wire from accidentally coming out of the path or channel. The entry point or entrance to the path or channel 212 is provided by the space or gap 214 between the fingers 206 and 208.

In order to minimize the crossing-diameter of the catheter 200, the fingers 206 and 208 of the connector are preferably dimensioned to keep their height or projection from the central longitudinal axis of the catheter 200 as short as possible, while still enabling the guide-wire portion 24A to be held securely in the path 212 for sliding movement resistant to accidental disconnection. Thus, in the preferred embodiment shown in the cross-sectional area of the channel 212 is just slightly larger than the outside diameter of the guide-wire 24A and the fingers are very thin.

The connection of the catheter 200 to the guide-wire portion 24A will now be described with reference to FIGS. 13 and 14. As before, it is assumed that the guide-wire 24 is already in place so that its distal end (not shown) is located at some internal situs within the body of the being, while its proximal end is located outside the body of the being, with the intermediate portion 24A of the guide wire also being located outside the body of the being distally of the proximal end of the guide-wire. As pointed out earlier while the portion 24A of the guide-wire is preferably outside the body of the being, such an arrangement is not required. In this regard in some medical applications the guide wire portion 24A where the catheter is to be connected may be located internally of the being and access provided to it via a natural body orifice or opening or through some surgically formed opening.

In any case, as best seen in FIG. 13 the catheter 202 is oriented so that the entry mouth or gap 214 of the path 212 at the distal end of the channel is aligned with the portion 24A of the guide-wire 24, e.g., the longitudinal axis of the guide-wire portion 24A is perpendicular to the longitudinal axis of the catheter 200 and is between the fingers forming the gap. Once so aligned the distal end of the catheter 20 is twisted about an axis perpendicular to the longitudinal axis of the catheter to bring the more distally located portion of the guide-wire portion 24A into the path 212 under the finger 206, while at the same time bringing the more proximally located portion of the guide-wire portion 24A into the path 212 under the finger 208 as shown in FIG. 14. This action completes the sliding securement of the catheter on the guide-wire 24. Therefore, once the sliding securement has been accomplished, the catheter 200 can be slid or moved in the distal direction along the guide-wire 24 to bring the open distal end 20E of the catheter to the desired position within the being's body, e.g., at a situs of the atherosclerotic deposit to be removed.

It should be pointed out at this juncture that while the foregoing discussion has described the twisting of the catheter or other tubular instrument with respect to the guide-wire or other elongated guide member to releasably secure the two together, that methodology is not the only method for achieving their releasably securement. Thus, as will be appreciated by those skilled in the art, the guide-wire or other elongated guide member can be twisted with respect to the catheter or other tubular instrument to cause the guide-wire or other tubular instrument to be introduced into the path for holding the two together.

It should also be pointed out that while the foregoing discussion has described catheters or other tubular instruments with the various types of connectors forming a portion thereof, it should be clear that connectors, per se, may be constructed in accordance for mounting, e.g., retrofitting, to existing catheters or other tubular instruments. Thus, the subject invention not only contemplates catheters or other elongated tubular instruments including connectors for connecting the catheters or other tubular instruments to guide-wires or other elongated guide member, but also contemplates connectors, per se, for use with conventional catheters to achieve those ends.

Without further elaboration the foregoing will so fully illustrate our invention that others may, by applying current or future knowledge, adopt the same for use under various conditions of service.

We claim:

1. A tubular instrument arranged to be used with a guide-wire or other elongated guide member, the guide wire or other elongated guide member having a distal end portion and a proximal end portion, the distal end portion of the guide-wire or other elongated guide member being arranged to be extended to some interior position within a lumen in the body of a living being, with the proximal end portion being located outside the body of the being, said tubular instrument having an end portion arranged to readily connect said instrument to said guide-wire or other elongated guide member so that said tubular instrument can be guided to a desired position within the body of the being along the guide-wire or other elongated guide member, said tubular instrument having a connector at said distal end, said connector establishing a helical path into which a portion of the guide-wire or other elongated guide member can be inserted from a lateral direction by a twisting action and retained therein without requiring access to either end of the guide-wire or other elongated guide member.

2. The instrument of claim 1 wherein said tubular instrument includes a hollow wall portion forming the distal end of said instrument, said hollow wall portion encircling a passageway and terminating at a distal opening, and wherein said helical path is a helical channel in said hollow wall portion and communicating with said passageway and said opening.

3. The instrument of claim 2 wherein said channel has a proximal end and a distal end in communication with said opening in said distal end of said instrument, and wherein said distal end of said channel is arranged to initially receive the guide-wire or other elongated guide member so that the guide-wire or other elongated guide member can be inserted into said channel.

4. The instrument of claim 3 wherein said channel is arranged so that when said instrument is in place on the guide-wire or other elongated guide member the guide-wire or other elongated guide member extends through said opening in said distal end of said instrument, through a portion of said passageway of said instrument, and out of said proximal end of said channel.

5. The instrument of claim 4 wherein said distal end of said channel is in the form of a flared mouth having a width greater than the width of said channel to facilitate the insertion of the guide-wire or other elongated guide member into said channel.

6. The instrument of claim 4 wherein said proximal end of said channel is in the form of window having a width greater than the width of said channel.

7. The instrument of claim 1 wherein said path is shaped to enable said instrument to be placed on the guide-wire or other elongated guide member and then twisted to insert the guide-wire into said path.

8. The instrument of claim 1 wherein said helical path is of a fixed or variable pitch.

9. The instrument of claim 8 wherein said instrument includes a hollow wall portion forming the distal end of said instrument, said hollow wall portion encircling a passageway and terminating at a distal opening, and wherein said helical path is a helical channel in said hollow wall portion and communicating with said passageway and said opening.

10. The instrument of claim 9 wherein said helical channel has a proximal end and a distal end in communication with said opening in said distal end of said instrument, and wherein said distal end of said helical channel is arranged to initially receive the guide-wire or other elongated guide member so that the guide-wire or other elongated guide member can be inserted into said helical channel.

11. The instrument of claim 10 wherein said channel is arranged so that when said instrument is in place on the guide-wire or other elongated guide member the guide-wire or other elongated guide member extends through said opening in said distal end of said instrument, through a portion of said passageway of said instrument, and out of said proximal end of said channel.

12. The instrument of claim 11 wherein said distal end of said channel is in the form of a flared mouth having a width greater than the width of said channel to facilitate the insertion of the guide-wire into said channel.

13. The instrument of claim 12 wherein said proximal end of said channel is in the form of window having a width greater than the width of said channel.

14. The instrument of claim 13 additionally comprising a depression in the wall of said instrument located immediately proximally of said window.

15. The instrument of claim 2 wherein said opening in said distal end of said instrument is beveled.

16. A connector for use with a tubular instrument to slidably mount said tubular instrument onto a guide-wire or other elongated guide member, the guide wire or other elongated guide member having a distal end portion and a proximal end portion, the distal end portion of the guide-wire or other elongated guide member being arranged to be extended to some interior position within a lumen in the body of a living being, with the proximal end portion being located outside the body of the being, said tubular instrument having an distal end portion at which said connector is arranged to be located, said connector establishing a path into which a portion of the guide-wire or other elongated guide member can be inserted from a lateral direction by a twisting action without requiring access to either end of the guide-wire or other elongated guide member.

17. The connector of claim 1 wherein said helical path comprises a channel having a proximal end and a distal end, and wherein said distal end of said channel is in the form of a flared mouth having a width greater than the width of said channel to facilitate the insertion of the guide-wire or other elongated guide member into said channel.

18. The connector of claim 1 wherein said helical path comprises a channel having a proximal end and a distal end, and wherein said proximal end of said channel is in the form of window having a width greater than the width of said channel.

19. The connector of claim 17 wherein said path is a helix of fixed or variable pitch.

20. The connector of claim 18 wherein the instrument includes a hollow wall portion forming the distal end of the instrument, the hollow wall terminating at a distal opening, and wherein said path is a helical channel in the hollow wall portion and communicating with the passageway and the opening.

21. The connector of claim 20 wherein said helical channel has a proximal end and a distal end in communication with the opening in the distal end of the instrument, and wherein said distal end of said helical channel is arranged to initially receive the guide-wire or other elongated guide member so that the guide-wire or other elongated guide member can be inserted into said helical channel.

22. The connector of claim 19 wherein said instrument has a distal opening, and wherein said channel is arranged so that when the instrument is in place on the guide-wire or other elongated guide member the guide-wire or other elongated guide member extends through the opening in the distal end of the instrument, through a portion of the instrument, and out of said proximal end of said channels.

23. The connector of claim 20 wherein said distal end of said channel is in the form of a flared mouth having a width greater than the width of said channel to facilitate the insertion of the guide-wire or other elongated guide member into said channel.

24. The connector of claim 21 wherein said proximal end of said channel is in the form of window having a width greater than the width of said channel.

25. The connector of claim 22 wherein said proximal end of said channel is in the form of a window, and additionally comprising a depression in the wall of said instrument located immediately proximally of said window.

* * * * *